(12) United States Patent
Koltermann et al.

(10) Patent No.: US 6,821,758 B1
(45) Date of Patent: Nov. 23, 2004

(54) METHOD FOR THE PRODUCTION OF BIOPOLYMERS WITH MODIFIED PROPERTIES

(75) Inventors: Andre Koltermann, Gottingen (DE); Ulrich Kettling, Gottingen (DE); Manfred Eigen, Gottingen (DE)

(73) Assignees: Max-Planck-Gesellschaft zur Forderung der Wissenschaften e.V., Berlin (DE); Direvo Biotech AG, Cologne (DE)

( * ) Notice: Subject to any disclaimer, the term of this patent is extended or adjusted under 35 U.S.C. 154(b) by 0 days.

(21) Appl. No.: 09/708,497

(22) Filed: Nov. 9, 2000

(30) Foreign Application Priority Data

Nov. 9, 1999  (DE) ......................................... 199 53 854

(51) Int. Cl.[7] .............................................. C12P 19/34
(52) U.S. Cl. .................................................... 435/91.1
(58) Field of Search ............................ 435/6, 7.1, 91.1, 435/91.2; 536/22.1, 23.1, 24.3–24.33

(56) References Cited

U.S. PATENT DOCUMENTS

| | | | |
|---|---|---|---|
| 4,959,312 A |   | 9/1990 | Sirotkin |
| 5,849,545 A |   | 12/1998 | Henco et al. |
| 6,080,544 A | * | 6/2000 | Weghorst et al. ............... 435/6 |
| 6,127,116 A | * | 10/2000 | Rice et al. ...................... 435/6 |

FOREIGN PATENT DOCUMENTS

| | | |
|---|---|---|
| EP | 0 9 11 396 A2 | 4/1999 |
| WO | WO9218645 | 10/1992 |
| WO | WO 95/08003 | 3/1995 |
| WO | WO9522625 | 8/1995 |
| WO | WO9720078 | 6/1997 |
| WO | WO9842728 | 10/1998 |
| WO | WO9858080 | 12/1998 |
| WO | WO 98/58080 | 12/1998 |
| WO | WO 99/29902 | 6/1999 |
| WO | WO9929902 | 6/1999 |
| WO | WO9934195 | 7/1999 |
| WO | WO00/14282 | * 3/2000 |
| WO | WO 00/58517 | 10/2000 |

OTHER PUBLICATIONS

Epicenter Catalog pp. 66,75 1998.*

(List continued on next page.)

*Primary Examiner*—Kenneth R. Horlick
(74) *Attorney, Agent, or Firm*—Birch, Stewart, Kolasch & Birch, LLP

(57) ABSTRACT

A method for the production of biopolymers with modified properties wherein at least one cycle comprising the following steps is completed:

(a) providing a population of single-stranded polynucleotide molecules, wherein individual polynucleotide molecules comprise homologous and heterologous sequence segments and wherein individual ones of said single-stranded polynucleotide molecules can form double-stranded polynucleotide molecules with other ones of said single-stranded polynucleotide molecules within said population;

(b) forming double-stranded polynucleotide molecules from the population of single-stranded polynucleotide molecules provided according to step (a) comprising double-stranded polynucleotide molecules with different heterologous sequence segments;

(c) partially and exonucleolytically degrading the single-strands of the double-stranded polynucleotide molecules produced according to step (b); and (d) temple-directed single-stand synthesizing the degraded ends of the partially degraded double strand produced according to step (c), wherein steps (c) and (d) may be carried out sequentially or contemporaneously.

31 Claims, 7 Drawing Sheets

OTHER PUBLICATIONS

Pandolfi, Daniela et al., "Evaluation of different types of end–capping . . . ", Database BIOSIS Online Bioscience Information Services, (1999) Databasae No. XP002174301 Abstract.

Kettling, Ulrich et al.; "Evolutionary Biotechnology . . . "; Current Topics in Microbiology and Immunology, vol. 243 Combinatorial Chemistry in Biology.

Koltermann, Andre et al.; "Principles and Methods . . . "; Biophysical Chemistry 66 (1997) 159–177.

Eigen, Manfred et al.; "Sorting single molecules . . . "; Proc. Natl. Acad. Sci. USA 91 (1994) pp. 5740–5747.

Zhao, Huimin et al. "Molecular evolution by staggered extension"; Nature Biotechnology vol. 16, Mar. 1998 pp. 258–261.

Shao, Zhixin et al.; "Random–priming in vitro . . . "; Nucleic Acid Research, 1998 vol. 26, No. 2 pp. 681–683.

Stemmer, William P.C.; "Rapid evolution of A . . . "; Nature vol. 370, Aug. 4, 1994 pp. 389–391.

Kolodner, Richard D. et al; "Eukaryotic DNA mismatch repair"; Curr. Opin. Genet. Dev. (1999), 9(1), 89–96 (Abstract).

Florentini, PAcla et al.; "Exonuclease I of Sacchararomyces . . . "; Molecular & Cellular Biology, 1997 vol. 17, No. 5, pp, 2764–2773 (Abstract).

* cited by examiner

| Isolate | Mutations | | | | | | | | | | | | |
|---|---|---|---|---|---|---|---|---|---|---|---|---|---|
| UJ02 | | | | | | | | | | | | | |
| UJ04 | G156A | | | | T303A | | A399 T448A | | | | | | |
| UJ10 | T46C A53T | | T200G | T261A | | C334T | | | | | | C717C T767C T780C | |
| UJ18 | | | | T270C | | | | T450G | | | | | |
| UJ21 | | | | | | T361C | | | | | | | |
| UJ25 | T148A | | A216T | | | | | T370A | T484A | | | | T785G |
| UJ26 | | T180C | | A256C | | | | | | T561A | | | |
| AA17 | | T180C | | A256C | | | | | | | A663G | | |
| AA18 | G156A | | | | | | | | T484A | G501A T508A | | | T785G |
| AA19 | | | | | | C334T | | | | | | | T785G |
| AA22 | | T180C | | A256C | | | | | | | | | |
| AA23 | | | A216T | | T303A | | A399G T448A | | | G501A T508A | | C717C T767C T780C | |
| AA25 | | | A216T | | T303A | | A399G T448A | | | | A663G | | |
| AA26 | T148A | | A216T | | | | | | | | | | T785G |
| AA30 | T146A | | A216T | | | | A399G T448A | | | C519A T561A | | T767C T780C | |
| AA33 | | | | | | | | T370A | T484A | | | C717C T767C T780C | |
| AA37 | T46C A53T | | | | | | | T370A | T484A | | | T780C | |
| AA41 | | | A216T | | | | | | | T561A | | | T785G |
| AA43 | | | | T261A | | C334T | | | | | | | |

Figure 6

METHOD FOR THE PRODUCTION OF BIOPOLYMERS WITH MODIFIED PROPERTIES

BACKGROUND OF THE INVENTION

The present invention relates to a method for the production of polynucleotide molecules with modified properties as well as to a kit containing instructions for carrying out said method.

Biomolecules—and, in particular, biopolymers such as polynucleotides, polypeptides, polysaccharides etc.—are not only the basis of biological life known to us but they are also used more and more in the most vaned technical fields of application. The search for new functional biomolecules, their isolation or production as well as their technical application is the subject-matter of modern biotechnology. Apart from incidentally finding so far unknown biomolecules in nature exhibiting desired properties (cf. natural substance screening), methods have emerged recently which imitate the principles of natural evolution in the laboratory and thus generate completely new biomolecules with specific properties (WO 92/18645; Eigen and Rigler, Proc. Natl. Acad. Sci. USA 91 (1994), 5740; Koltermann and Kettling, Biophys. Chem. 66 (1997), 159; Kettling et al., Current Topics in Microbiol. & Immunol. 243 (1999), 173). This so-called evolutionary biotechnology or directed molecular evolution takes the findings from theoretical and practical evolution research carried out over many years and applies them to the directed evolution of biomolecules.

Put very simply, directed evolution of molecular functions takes place by effective interaction of variation and selection processes acting on molecule populations. While variation starts out from the information content of a biomolecule, selection takes place by means of the molecular phenotype. Information of a polynucleotide molecule (genotype) denotes the sequential order of various monomers in a polynucleotide molecule. The phenotype of a polynucleotide molecule denotes the sum of the functions and properties of a polynucleotide molecule and of the transcription or translation products encoded by a polynucleotide. The linkage of sequence information and selectable phenotype can be achieved either by amplification linked selection (Kettling, PhD thesis, Göttingen/TU Braunschweig (1999)), by compartmentation and functional analysis, called screening (WO 92/18645; WO 99/34195) or by physical linkage of genotype and phenotype as well as their selection (DE 196 46 372; U.S. Pat. No. 5,849,545; DE-A1 43 056 51).

The kind of interaction of variation and selection processes are crucial for the success of directed evolution strategies. In nature as well as in the laboratory the quasi-species principle has proven to be the most successful strategy—measured by the time needed for an evolutionary generation and optimization of molecular functions. Quasi-species denotes a dynamic population of related molecule variants (mutants) resulting from erroneous replication. It could be shown that—corresponding to the quasi-species principle—not the wild type (centre of the quasi-species) but the whole spread is object of selection. Under modified selection conditions advantageous variants are already present in such a mutant distribution corresponding to their fitness value and do not have to be formed by subsequent, random mutations. If the selection parameters are changed the evolutionary generation resembles an implicitly directed drift of the quasi-species along the edges of the fitness landscape. The production of quasi-species and the application of this principle for evolutionary biotechnology is described in WO 92/18645.

The basis for the production of a quasi-species is an erroneous replication of the molecule variants. When polynucleotides are used replication preferably takes place by means of replication enzymes, i.e. polymerases which make the template-directed synthesis of a polynucleotide molecule possible. The introduction of errors, i.e. the variation of the molecule information, can be achieved by the inherent erroneous copying process alone, but also by the purposeful increase of the inaccuracy of the polymerase (e.g. defined non-balanced addition of the monomers, addition of base analogues, erroneous PCR, polymerases with very high error rate), by chemical modification of polynucleotides after synthesis, by the complete synthesis of polynucleotides under at least partial application of monomer mixtures and/or of nucleotide analogues as well as by a combination of these methods.

Apart from these methods to create punctual mutations (in the form of base exchanges, deletion and insertion) the recombination of sequence parts in nature is a very successful strategy for combining punctual mutations but also for combining domains within a polymer, for combining subunits of a heteromultimer or for combining gene variants within a gene cluster or a genome. Homologous recombination, in particular, i.e. the combination of corresponding sequence parts from different variants while maintaining orientation and reading frame plays an important role since the background noise of unrelated sequences that accompanies an unspecific recombination can be prevented. According to the quasi-species principle, homologous recombination is a purposeful means to expand the sequence distribution. Various related sub-distributions of a quasi-species which originate from the underlying fitness landscape but which have such a low relative degree of relatedness that converging along the edges of the fitness landscape is very unlikely without recombination, can be expanded tremendously by homologous recombination. Thereby, an evolutionary method emerges which, in contrast to serial introduction of mutations, leads to a multiplication of the experimental speed. Furthermore, a technologically controlled application of homologous recombination, in principle, also allows for the fusion of quasi-species distributions which were generated under different selection pressure and, thus, for the fusion of separately selected molecular functions.

In experiments, recombination can be conducted in different ways: on the one hand in vitro using individual enzyme functions or defined mixtures or sequences of enzymatic processing steps, on the other hand, in vivo using cellular recombination and/or repair processes.

For in vitro methods, mainly PCR based methods have technically been used so far. First to mention is DNA shuffling, also called sexual PCR (WO 95/22625: Stemmer, Nature 370 (1994), 389). In this method any overlapping gene fragments are provided and subsequently assembled into products of original length by a PCR without addition of a primer. Thus, the mutual priming of the fragments in each PCR cycle allows for fragments of different origin to be incidentally linked to form a product molecule in a homologous way. By adjusting the fragment length DNA shuffling makes it possible, at least in principle, to limit the frequency of recombination events. Another PCR-based method is the method of PCR using random primers (WO 98/42728); Shao et al., Nucl. Acids Res. 26 (1998), 681). In this method primers with randomized sequences are used which enable a start of polymerization at random positions within a polynucleotide. Thus, similar to DNA shuffling, short polynucleotide fragments are formed which can recombine with each other by mutual priming. With this method controlling of the recombination frequency is hardly possible. Moreover, unspecific primers lead to a comparatively high inherent error rate which can constitute a problem with sensitive sequence parts and/or long genes. Alternatively to these methods, the staggered extension process (WO 98/42728; Zhao et al., Nat. Biotechnol. 16 (1998), 258) uses a modified PCR protocol to provoke a strand exchange to take place during the PCR amplification. Using very short phases at the polymerization temperature between the melting and annealing phase allows for incompletely formed products to hybridize to new templates and to be prolonged further. Adjustment of the recombination frequency can take place by setting the polymerization time and the number of cycles. A technical limit, however, is the exact adjustment of very short phases to a certain temperature. Alternatively to this PCR-based method, a method has been described which produces heteroduplexes from a population of polynucleotide sequences with mutations which are then subjected to a statistic repair in vivo by introduction into cells or in vitro by incubation with a cell extract, leading, to a certain extent, to the formation of recombinant molecule variations depending on the relative frequency of variants in the initial population (WO 99/29902). The use of cellular repair systems specifically recognising unpaired bases and statistically repairing one of the two strands of the double strand is characteristic of this method. This method is restricted, on the one hand, by the limited efficiency in introducing polynucleotides into cells and, on the other hand, by the lack of controllability of the repair processes.

Thus, the technical problem underlying the present invention is to provide a method for the production of polynucleotides with modified properties avoiding the above-described disadvantages of the known methods and making an efficient new combination of genotypes of a quasi-species of polynucleotide molecules possible, which then leads to the formation of modified phenotypes. Especially, the technical problem is to provide an in-vitro homologous recombination method that combines a precise controllability of the number of recombination events with the possibility of a regio-selective recombination.

This technical problem has been solved by providing the embodiments characterized in the claims.

DETAILED DESCRIPTION OF THE INVENTION

Therefore, the present invention relates to a method for the production of polynucleotide molecules with modified properties, wherein at least one cycle comprising the following steps is completed:

(a) providing a population of single-stranded polynucleotide molecules, wherein the individual polynucleotide molecules of said population have at least one homologous sequence segment and at least two heterologous sequence segments and wherein in the population also strands are contained that are each completely or partially complementary to these single strands;

(b) formation of double-stranded polynucleotide molecules of the population of single-stranded polynucleotide molecules provided according to step (a) comprising double strands with different heterologous sequence segments (heteroduplexes);

(c) partial exonucleolytic single-strand degradation of the double-stranded polynucleotide molecules produced according to step (b); and (d) template-directed single-strand synthesis starting from the degraded ends of the partially degraded double strand produced according to step (c), wherein steps (c) and (d) may be carried out subsequently or contemporaneously.

FIG. 1 shows schematically one of the possible variants of the method which will be described below.

Depending on the requirements, the method of the invention permits both an incidental and a controlled new combination of heterologous sequence segments. The principle of a defined-partial sequential single-strand polynucleotide degradation of double-stranded heteroduplex polynucleotides and subsequent semi-conservative polymerization of single-stranded polynucleotides permits—apart from complete recombination—also a regio selective recombination of heterologous sequence segments. In addition, the frequency of recombination is high and can be precisely adjusted by the number of cycles. Such a control of the recombination frequency may also be achieved in part by means of the so far described methods DNA shuffling and staggered extension process. Random priming does not offer this possibility, the repair system only hardly offers it. Just like random priming, the staggered extension process has the disadvantage of having a background of non-recombined starting polynucleotides since both methods are based on an amplification of these starting polynucleotides. Although DNA shuffling has a reduced background of starting polynucleotides, this is achieved by the fragmentation of starting sequences which process requires very sophisticated experiments. Furthermore, as random priming and repair system, it does not offer any possibility of a regio selective recombination. Hence, the method of the invention is characterised by a combination of advantages which could not be achieved with any of the methods described so far (cf. Table 1). Further advantages of the method are the fact that it entails less sophisticated experiments and less time and offers the possibility of automation.

TABLE 1

Comparison of various in vitro recombination methods

| various in vitro recombination methods: | present invention embodiment: | | DNA-shuffling | staggered extension | random priming | repair system |
|---|---|---|---|---|---|---|
| advantages: | A | B | | | | |
| high probability of recombination | + | + | + | − | + | − |
| control of the frequency of recombination | + | + | +/− | + | − | +/− |

TABLE 1-continued

Comparison of various in vitro recombination methods

| various in vitro recombination methods: | present invention embodiment: | | DNA- shuffling | staggered extension | random priming | repair system |
|---|---|---|---|---|---|---|
| advantages: | A | B | | | | |
| regio complete recombination possible | + | + | + | + | + | +/− |
| regio selective recombination possible | + | + | − | + | +/− | − |
| recombination of the initial population | + | + | + | − | − | +/− |
| no fragmentation of the starting sequences | + | + | − | + | + | + |
| entailing less sophisticated experiments and less time | + | + | − | + | + | +/− |
| can be automated | + | + | − | + | + | +/− |

Products resulting from each individual cycle according to the method of the invention are semi-conservative, single-stranded polynucleotides since—depending on the embodiment—a longer or shorter sequence segment was maintained at the 3'- or 5'-end while the rest of the sequence was synthesized anew at the 3'- or 5'-end.

In a preferred embodiment, more than one cycle comprising the aforementioned steps (a) to (d) is completed, i.e. at least two, preferably at least five, more preferably at least ten and most preferably at least twenty.

The cyclic application of the method of the invention makes it possible for polynucleotides with multiple newly combined sequence segments to be generated from a starting pool of related polynucleotide sequences. In particular, the cyclic application makes it possible to combine several heterologous sequence segments with each other. Moreover, it is possible to exactly control the recombination frequency for each polynucleotide strand by the number of cycles. With cyclic application, also the average distance between the new combinations can be controlled from one cycle to the next.

In a preferred embodiment, the degradation length of the exonucleolytic degradation according to step (c) of the method of the invention gets shorter when the number of cycles increases. This allows for a new combination in the entire region of the sequence of the polynucleotides provided according to step (a).

In a particularly preferred embodiment of the method of the invention, the regio selectivity of the combination of partially degraded and newly synthesized strands is regulated through the control of the partial, exonucleolytic single-strand degradation according to step (c) of the method.

In another preferred embodiment, a selection step is carried out after one, several or all cycles of the method of the invention. This selection step may be related either to the genotype or to the phenotype or to both the genotype and the phenotype of the polynucleotide.

In this case, the genotype of a polynucleotide is the sequential order of different monomers in the polynucleotide. The phenotype is the sum of functions and properties of a polynucleotide molecule and of the transcription or translation products encoded by a polynucleotide.

The selection step may be carried out by methods known to the person skilled in the art, for instance, by amplification-coupled (natural) selection, selection by physical separation or selection by screening (Koltermann and Kettling, Biophys. Chem. 66 (1997), 159; Kettling et al., Current Topics in Microbiol. and Immunol. 243 (1999), 173).

The population of single-stranded polynucleotide molecules provided according to step (a) of the method of the invention can be any population of single-stranded polynucleotide molecules comprising at least two kinds of polynucleotide molecules, wherein these comprise at least one homologous sequence segment and at least two heterologous sequence segments. The term "population of single-stranded polynucleotide molecules" means a range of polynucleotide molecules, wherein intermolecular interactions in the form of specific base pairings between the molecules are prevented or do not exist. The term "polynucleotides" (nucleic acids, oligonucleotides) comprises both DNA and RNA. Polynucleotides are linear, orientated (5'-3'-direction) heteropolymers which may be either single-stranded or double-stranded. In the double strand, two single strands are linked by means of interactions in the form of specific base pairings. In principle, the polynucleotides can also be DNA or RNA with modified monomers. In general, the method may be used for similarly constructed, artificial polymers, too.

The term "homologous segments" denotes segments which are identical or complementary on one or more polynucleotide molecules, i.e. which have the same information at the corresponding position.

The term "heterologous segments" means segments which are not identical or complementary on two or more polynucleotide molecules, i.e. which have different information at the corresponding position. Information of a polynucleotide molecule (genotype) is the sequential order of various monomers in a polynucleotide molecule. A heterologous sequence segment has a length of at least one nucleotide, may, however, also be much longer. In particular, a heterologous sequence segment may have a length of two nucleotides or three nucleotides, e.g. a codon, and, preferably, of more than 5 nucleotides, most preferably of more than 10 nucleotides. In principle, there is no upper limit as regards the length of the heterologous segment. Nevertheless, the length of a heterologous segment should not exceed 10,000 nucleotides, preferably it should not be longer than 5,000 nucleotides, more preferably not longer than 2,000 nucleotides and most preferably not longer than 1,000 nucleotides. Such longer sequence segments may, for example, be the hypervariable regions of a sequence encoding an antibody, domains of a protein, genes in a gene cluster, regions of a genome, etc. Preferably, the heterologous segments are sequence segments in which the polynucleotide molecules differ in single bases. Heterologous segments, however, may also be based on the fact that a deletion, duplication, insertion, inversion, addition or similar is present or has occurred in a polynucleotide molecule.

According to the invention, the polynucleotide molecules provided according to step (a) of the method of the invention have at least one homologous and at least two heterologous sequence segments. Preferably, however, they have a plurality of homologous and heterologous segments. In principle, there is no upper limit to the number of homologous and heterologous segments.

The heterologous segments in the single-stranded polynucleotide molecules are each interrupted by homologous segments. The homologous segments preferably have a length of at least 5, more preferably of at least 10 and most preferably of at least 20 nucleotides. Like the heterologous segments, the homologous segments, too, may be much longer and, in principle, there is no upper limit to their length. Preferably, their length should not exceed 50,000 nucleotides, more preferably, they should not be longer than 20,000 nucleotides, even more preferably not longer than 10,000 nucleotides and most preferably not longer than 1,000 nucleotides.

The population of single-stranded polynucleotide molecules also contains strands that are wholly or partially complementary to the single strands. The term "complementary" denotes segments on two or more polynucleotide molecules which, due to their information, may lead to the formation of double strands restricted to these segments by means of interaction in the form of specific base pairings.

The providing of single-stranded polynucleotide molecules according to step (a) of the method of the invention can be conducted by means of methods known to the person skilled in the art. These include, for instance, physical, chemical, biochemical and biological methods. Examples of these include the melting of polynucleotide double strands by means of heating to temperatures higher than the annealing temperature (Newton, in: PCR, Spektrum Akademischer Verlag (1994); Lazurkin, Biopolymers 9 (1970), 1253–1306); denaturation of polynucleotide double strands by means of adding denaturation agents (urea, detergents, etc.); addition of enzymes which convert double-stranded polynucleotides into single-stranded polynucleotides, e.g. by means of exonucleolytic degradation of double-stranded DNA to single-stranded DNA or by means of synthesis of single-stranded RNA using a DNA-dependent RNA polymerase with or without reverse transcriptase; asymmetric PCR (Newton, in: PCR, Spektrum Akademischer Verlag (1994)), in which preferably one of the two product strands is formed by using an excess of one of the two primers; addition of proteins or enzymes which unwind double-stranded DNA molecules (gyrases, etc.) and other proteins or other agents which stabilise the developing single-stranded DNA molecules (single-strand binding protein, dendrimers, etc.) and insertion of the sequence into the genome of single-stranded viruses (M13, fd, etc.) and subsequent purification of the single-stranded polynucleotide genome (Trower, Methods in Mol. Biol. 58 (1996), 363–366; Ausubel, Current Protocols in Molecular Biology, Wiley (1987); Sambrook, Molecular Cloning, Cold Spring Harbor Laboratory Press (1989)). The skilled person is familiar with further methods such as the chemical synthesis of single-stranded polynucleotide molecules.

In a particularly preferred embodiment of the method of the invention related polynucleotide sequences of the distribution of mutants of a quasi-species are used for providing a population of single-stranded polynucleotides with homologous and heterologous segments (step (a), FIG. 1). In this context, the term "related" means polynucleotides which have both homologous and heterologous segments among each other.

A quasi-species is a dynamic population of related molecule variants (mutants) which is formed by faulty replication. It could be shown that, corresponding to the quasi-species principle, it is not the wild type (centre of the quasi-species) but the entire distribution that is the object of the selection. Under modified selection conditions, advantageous variants in such a distribution of mutants are already contained according to their fitness value and do not have to be formed by subsequent, random mutations first. If the selection parameters are changed successively, the evolutionary generation resembles an implicitly directed drift of the quasi-species along the edges of the fitness landscape. The production of quasi-species and the application of this principle for evolutionary biotechnology is described in WO 92/18645.

The basis for the production of a quasi-species is an erroneous replication of the molecule variants. When polynucleotides are used replication preferably takes place by means of replication enzymes, i.e. polymerases which make the template-directed synthesis of a polynucleotide molecule possible. The introduction of errors, i.e. the variation of the molecule information, can be achieved by the inherent erroneous copying process alone, but also by the purposeful increase of the inaccuracy of the polymerase (e.g. defined non-balanced addition of the monomers, addition of base analogues, erroneous PCR, polymerases with very high error rate), by chemical modification of polynucleotides after synthesis, by the complete synthesis of polynucleotides under at least partial application of monomer mixtures and/or of nucleotide analogues as well as by a combination of these methods.

Preferably, distributions of mutants of a quasi-species are used, with the individual mutants of the quasi-species already being improved in their phenotypic properties of a desired molecular function in comparison to the wild type. The term "phenotype of a polynucleotide molecule" denotes the sum of functions and properties of a polynucleotide molecule and of the transcription or translation products encoded by a polynucleotide.

Furthermore, sequences of varied origin may be used, among others polynucleotide sequences of a gene family of different species, polynucleotide sequences which have been replicated in vivo (e.g. by viruses, by mutator bacteria, by bacteria under UV irradiation, etc.) or in vitro (e.g. by means of Qβ-replicase reaction, faulty PCR, etc.) with a particularly high rate of error, polynucleotide sequences in which, after the synthesis, mutations have been inserted by means of chemical agents or which have been chemically synthesized in such a way that they exhibit homologous and heterologous segments, or polynucleotide sequences which have been produced by combining the aforementioned techniques.

In principle, the polynucleotides used in the method of the invention may be any polynucleotides, in particular DNA or RNA molecules. Especially in step (b) of the method also double strands can be produced consisting of DNA and RNA strands (DNA/RNA hybrids).

The production of double-stranded heteroduplex polynucleotides (heteroduplexes) according to step (b) of the method of the invention is preferably achieved by hybridization of the homologous segments of the complementary single-stranded polynucleotides (Newton, in: PCR, Spektrum Akademischer Verlag (1994)).

The term "heteroduplexes" means polynucleotide double strands with at least one homologous and at least one heterologous segment. By using a population of polynucleotide sequences with heterologous segments, heteroduplexes are formed with a statistical probability which corresponds to the relative frequency of sequence variants. Starting out, for example, from an ideally mixed population in which two heterologous segments are present in two different variants each in equal shares, a heteroduplex statistically occurs with every second double-stranded polynucleotide. If the number of variants is markedly higher than the relative frequency of individual variants, heteroduplexes are formed almost exclusively.

Hybridization of the complementary single-stranded polynucleotides to form double-stranded polynucleotides is carried out according to methods known to the person skilled in the art. In particular, it can be achieved by combining the single strands and adjusting reaction conditions which promote the annealing of complementary polynucleotides, e.g. by lowering of the temperature, adjusting of a neutral pH value and low salt concentration, etc.

By means of the exonucleolytic degradation of the single strands of the heteroduplex polynucleotides according to step (c) of the method of the invention, the individual polynucleotide molecules now forming part of a double strand are exonucleolytically degraded in part. It is essential that there is only a partial exonucleolytic degradation. The exonucleolytic degradation of the double-stranded polynucleotide molecule can take place in 3'-5'-direction or in 5'-3'-direction or both in 3'-5'-direction and 5'-3'-direction. Moreover, the degradation of longer unpaired single-stranded sections of heterologous segments of the polynucleotide molecules may take place exonucleolytically by adding single-strand specific exonucleases both in 5'-3'- and in 3'-5'-direction. In this way, double-stranded polynucleotides with single-stranded sections are formed. The average length and the accompanying distribution of the single-strand degradation in 3'-5'-direction or 5'-3'-direction may also be controlled via the reaction conditions and the reaction time of the exonucleolytic degradation. In the case of regio selective recombination, the degradation reactions are intended to start and stop as simultaneously as possible, whereas in the case of complete recombination start and stop of the degradation reaction can also take place consecutively. Furthermore, a statistic single-strand degradation may be achieved, too, by inserting thioester instead of phosphodiester in the synthesis of single-stranded polynucleotides, with the exonucleolytic degradation of the single strand stopping at the first thioester each.

There is a plurality of exonucleases known that permit a 3'- or 5'-exonucleolytic degradation. In the early seventies various exonucleases were already isolated and described (Lehmann, in: The Enzymes, Boyer (Ed), Academic Press (1971), 251–270). Currently, a vast number of different exonucleases of the most varied organisms and with very different functions has been described (Koonin, Curr. Biol. 7 (1997), R 604–6). In general, exonucleases are involved in a multitude of different cellular processes. The most varied exonucleolytic activities have been described in the technical literature, e.g. the nucleolytic degradation of single-stranded DNA or RNA, both from the 3'- to the 5'-end of a polynucleotide and vice versa. Single strands in double-stranded DNA, too, can be degraded by exonucleases both from the 3'- to the 5'-end of a polynucleotide and vice versa. Even the exonucleolytic degradation of a double-stranded DNA, i.e. the simultaneous degradation of the 5'- and 3'-ends at a double-stranded end, has been described.

Some of these enzymes are already commercially available. Substitutionally for a plurality of exonucleases, exonuclease III (ExoIII) (E.C.3.1.11.2) is stated here as an example of the class of exonucleolytic enzymes. ExoIII is traded, for instance, by USB, Roche Molecular Biochemicals, Stratagen, New England Biolabs. ExoIII of E. coli has various activities. The enzyme is non-processive and has a specific 3'-5'-exonucleolytic activity at DNA double-strands, a DNA 3'-phosphatase activity and an endonucleolytic activity at apurinic sites in the DNA. ExoIII preferably degrades 3'-ends in DNA double-strands, whereas overhanging 3-ends are not degraded. Rogers and Weiss (Gene 11 (1980), 187–195), Rogers and Weiss (Methods Enzymol. 65 (1980), 201–211), Sambrook (ibid.), Henikoff (Gene 28 (1984), 351–359), Ljunquist et al. (J. Bacteriol. 126 (1976), 646–653), Vandeyar et al. (Gene 65 (1988), 129–133) and Guo and Wu (Nucl. Acids Res. 10 (1982), 2065–2084) give an overview of the isolation and characterisation of ExoIII. The skilled person also knows the most varied technical applications of ExoIII, e.g. in the formation of single-stranded templates for labelling processes (James and Leffak (Anal. Biochem. 141 (1984), 33–37)) and various sequencing techniques (Smith (Nucl. Acids Res. 6 (1979), 831–848), Guo and Wu (Methods Enzymol. 100 (1983), 60–96) and Hoheisl and Pohl (J. Mol. Biol. 193 (1987), 447–464)) and in the production of DNA fragments by means of inserted α-thiophosphate nucleotides in DNA and their terminated degradation by Exo III for sequencing reactions (Putney et al. (Proc. Natl. Acad. Sci. USA 78 (1981), 7350–7354) and Labeit et al. (DNA 5 (1986), 173–177)). The introduction of single-strand segments in double-stranded DNA and their treatment with mutagens (Shortle and Nahtans (Proc. Natl. Acad. Sci. USA 75 (1978), 2170–2174)) or the hybridization to faulty oligonucleotides (Nakamaye and Eckstein (Nucl. Acids Res. 14 (1986), 9679–9698)) lead to mutagenized segments in specific regions. Many other technical applications of ExoIII for the modification of DNA have been described in the technical literature (Masamune et al. (J. Biol. Chem. 246 (1971), 2680–2691), Luckow et al. (Nucl. Acids Res. 15 (1987), 417–429), Roberts et al. (Proc. Natl. Acad. Sci. USA 76 (1979), 760–764), Sakonju et al. (Cell 19 (1980), 13–25), Peters and Baumeister (J. Bacteriol. 167 (1986), 1048–1054), Garon et al. (Proc. Natl. Acad. Sci. USA 72 (1975), 3039–3043), Riley and Weintraub (Cell 13 (1978), 281–293), Wu (Nature 371 (1985), 84–87), Henikoff (ibid.), Hoheisl and Pohl (Nucl. Acids Res. 14 (1986), 3605) and Henikoff (Nucl. Acids Res. 18 (1990), 2961–2966)). Commercially available exonucleases are also DNA-polymerase-III-subunit-epsilon of E. coli with 3'-5'-exonucleolytic activity (Krutyakov (Mol. Biol. 32 (1998), 197–199)), lambda exonuclease by New England Biolabs of the coli phage lambda with lambda-5'-3'-exonucleolytic activity at double-stranded 5'-phosphorylated DNA, wherein non-phosphorylated 5'-ends in double strands and single-stranded DNA are degraded, too, but with a strongly reduced activity. Lambda exonuclease does not exhibit any activity at nicks or single-stranded segments in double-stranded DNA (Little (Gene Amplification & Analysis 2 (1981), 135–145)). Bal31 nuclease by USB, New England Biolabs and Quantum Biotechnologies is produced from the culture medium of *Alteromonas espejiana* Bal31. Bal31 degrades double-stranded DNA both from the 5'- and the 3'-ends and has, in addition, an endonucleolytic activity at single-stranded DNA (Gray et al. (Nucl. Acids Res. 2 (1975), 1459–1492), Legerski et al. (Nucl. Acids Res. 5 (1978), 1445–1464). Wei et al. (J. Biol. Chem. 258 (1983), 13506–13512), Sambrook (ibid.), Bencen et al. (J. Biol. Chem. 259 (1984), 13584–13589), Hauser & Gray (Genetic Analysis, Techniques & Applications 8 (1991), 139–147) and Zhen et al. (Biochemistry 25 (1986), 6598–6603)). Exonuclease I (ExoI) is traded by USB and is derived from *E. coli*. ExoI specifically degrades single-stranded DNA processively in 3'-5' direction (Brody et al. (J. Biol. Chem. 261 (1986), 7136–7143), Brody and Doherty (Biochemistry 24 (1985), 2072–2076), Philips and Kushner (J. Biol. Chem. 262 (1987), 455–459), Prasher et al. (J. Biol. Chem. 258 (1983), 6340–6343), Prasher et al. (J. Bacteriol. 153 (1983), 903–908) and Ray et al. (J. Biol. Chem. 249 (1974), 5379–5381)). Further commercially available exonucleases include exonuclease V (EC 1.3.1.11.5) by USB derived from *Micrococcus luteus* (ATCC 4698), exonuclease VII by USB derived from *E. coli*, T7-5'-exonuclease, Gene 6 by USB derived from the bacteriophage T7 and the T5-5'-exonuclease derived from the bacteriophage T5 (Sayers and Eckstein (J. Biol. Chem. 265 (1990), 18311–18317), Garforth et al. (Proc. Natl. Acad. Sci. USA 96 (1999), 38–49) and Moyer and Rothe (J. Virol. 24 (1977), 177–193)).

A great number of exonucleases that are not commercially available but accessible to the person skilled in the art via standard methods of biochemistry and molecular biology have also been described in the technical literature, e.g. the 3'-5'-exonucleases YNT20 from *Saccharomyces cerevisiae* (Hanekamp and Thorsness (Current Genetics 34 (1999), 438–448)), human WNR (Kamath-Loeb et al. (J. Biol. Chem. 273 (1998), 34145–34150), Huang et al. (Nat. Genet. 20 (1998), 114–116)), p53 from various organisms (Mummenbrauer et al. (Cell 85 (1996), 1089–1099), Janus et al. (Mol. Cell. Biol. 19 (1999), 2155–2168)), 3'-5'-exonuclease from B-lymphocytes (Kenter and Tredup (Mol. Cell. Biol. 11 (1991), 4398–4404)), TREX1 and TREX2 from mammals (Mazur and Perrino (J. Biol. Chem. 274 (1999), 19655–19660)), human Mre 11 (Paull et al. (Molecular Cell 1 (1998), 969–979)), 3'-5'-exonuclease from human myeloblasts (Perrino et al. (J. Biol. Chem. 269 (1994), 16357–16363)), 3'-5'-exonuclease from the cytosol of human acute lymphoblastic leukaemia H9 cells (Skalski et al. (Biochemical Pharmacology 50 (1995), 815–821)) and human VDJP (Zhu and Halligan (Biochem. Biophys. Res. Commun. 259 (1999), 262–270)). A vast number of 5'-3'-exonucleases, too, have been described in the technical literature and are accessible to the person skilled in the art via standard methods of biochemistry and molecular biology, e.g. DNase VII from human placenta nuclei (Pedrini and Grossman (J. Biol. Chem. 258 (1983), 1536–1543)), 5'-3'-exonuclease from the bacteriophage N4 (Guinta et al. (J. Biol. Chem. 261 (1986), 10736–10743)), exonuclease V from the nuclei of *Saccharomyces cerevisiae* (Burgers et al. (J. Biol. Chem. 263 (1988), 8099–8105)), exonuclease from calf thymus (Siegal et al. (Proc. Natl. Acad. Sci. USA 89 (1992), 9377–9381), Murante et al. (J. Biol. Chem. 269 (1994), 1191–1196)), 5'-3'-exonuclease from nuclear extracts (ExoI) from *Saccharomyces cerevisiae* (Huang and Symington (Mol. Cell. Biol. (1993), 3125–3134; Fiorentini et al. (Mol. Cell. Biol. 17 (1997), 2764–2773)), RAD2 and RTH1 from *Saccharomyces cerevisiae* as well as the human XPG homologue (Habroken et al. (J. Biol. Chem. 269 (1994), 31342–31345), Sommers et al. (J. Biol. Chem. 270 (1995), 4193–4196)), viral polymerase-associated exonucleases (Sayers (Methods Enzymol. 275 (1996), 227–238)), T4-RNase H from the bacteriophage T4 (Mueser et al. (Cell 85 (1996), 1101–1112)), as well as human Werner-Syndrome helicase (Suzuki et al. (Nucl. Acids Res. 27 (1999), 2361–2368)). In addition, use can also be made of the exonucleolytic activities of polymerases described below.

In a preferred embodiment of the method of the invention the exonucleolytic single-strand degradation of the double-stranded polynucleotides according to step (c) of the method of the invention is carried out in 3'-5' direction.

In a particularly preferred embodiment (embodiment A; cf. FIG. 2, first cycle), one strand of the double strand is protected from the exonucleolytic degradation so that in this embodiment only one of the two polynucleotide strands is subjected to exonucleolytic digestion while the complementary strand serves as template in the template-directed single-strand synthesis according to step (c).

In another preferred embodiment both polynucleotide strands are subjected to exonucleolytic digestion (embodiment B, FIG. 3, first cycle) so that both strands are used with a part of their sequence as template while the other part of the sequence goes through a semi-conservative single-strand synthesis.

The exonucleolytic degradation of single-stranded polynucleotides in the heteroduplex polynucleotides produced according to step (c) can be carried out according to methods known to the person skilled in the art and has been described, for instance, in Ross (Methods 17 (1999), 52–59; Hoheisel (Anal. Biochem. 209 (1993), 238–246) and Ausubel (Current Protocols in Molecular Biology; Wiley (1987)).

In particular, chemical or biochemical methods are used. The exonucleolytic degradation is preferred to be carded out in a biochemical manner by means of enzymes having a corresponding specific activity, e.g. a 3'-exonucleolytic degradation using exonuclease III from *E. coli*. The length of the degradation and thus the regio selectivity of the new combination can be influenced to a crucial extent via the reaction conditions and the reaction time of the partial degradation. The reaction can be started e.g. by changing the buffer conditions or the temperature, by adding a co-factor, preferably, however, by adding exonuclease and can be stopped, for instance, by changing the buffer conditions, by adding an inhibitor or a protease, by lowering the temperature, preferably, however, by raising the temperature (e.g. denaturation of exonuclease III at 62° C.). The rate of degradation of the exonuclease depends mainly on the reaction conditions and can also be adjusted in a broad range. If the rate of degradation of exonuclease III, for instance, is 400 nucleotides, or preferably 25 nucleotides, per minute under certain reaction conditions, the range can be adjusted by selecting the incubation time, e.g. with an accuracy ranging between 20–30 nt. It is general knowledge of the person skilled in the art to adjust the different conditions to control the exonucleolytic degradation, as shown for example in Example 2 and FIG. 8.

Alternatively, the 3'-5' exonucleolytic activity can also be provided by the polymerase used in step (d) in so far as this polymerase can perform the corresponding exonuclease function.

As regards embodiment A shown in FIG. 2, in which one strand is protected from the 3'-exonucleolytic degradation, there are various ways to protect the 3'-ends from exonucleolytic degradation, e.g. by inserting a thioester instead of a phosphodiester at the 3'-end of the phosphoribose backbone. In the case of a two-sided thioester modification, by prior insertion of a singular restriction site in the sequence and subsequent cleavage with the restriction enzyme one of the two strands can be selectively protected (embodiment A-1). Furthermore, one strand can be protected by first providing one of the two strands as circular single strand (e.g. by using a viral single-strand genome, embodiment A-2) or by producing a single-stranded 3'-overhang of more than 4 bases (i.a. possible if exonuclease III is used, embodiment A-3). Moreover, by means of ligase, both ends on one side of the double strand can be covalently joined by attaching a circular single strand (embodiment A-4).

In another preferred embodiment of the method according to the invention, unpaired segments of the heteroduplexes are degraded exonucleolytically in step (c) by means of single-strand specific exonuclease, e.g. in 3'-5' direction by exonuclease I from *E. coli*.

In another variant of the method of the invention, the exonucleolytic single-strand degradation of the double-stranded polynucleotide molecules according to step (c) is carried out in 5'-3' direction. Preferably, the T7-exonuclease Gene 6 from the bacteriophage T7 is used.

Moreover, in a preferred embodiment, unpaired segments of the heteroduplexes are exonucleolytically degraded in 5'-3' direction, e.g. by means of the exonuclease VII from *E. coli*. In addition, a 5'-end of the polynucleotide double-strand is preferred to be modified in such a way that it is protected from the 5'-exonucleolytic single-strand degradation.

In another preferred embodiment of the method of the invention, single-strand nicks are inserted in the double-stranded polynucleotide molecules before the exonucleolytic single-strand degradation according to step (c) of the method of the invention takes place (embodiment C, FIG. 4, first cycle). On average, there is one or less than one single-strand nick per double-stranded polynucleotide molecule. Single-strand nicks can be inserted, for example, by sequence-specific nicking enzymes. Examples of such nicking enzymes are the nicking enzymes V.BchI from *Bacillus chitinosporus*, N.BstNBI from *Bacillus stearothermophilus*, N.BstSEI from *Bacillus stearothermophilus*, N.CviPII from Chlorella strain NC64A, N.CviQXI from Chlorella strain NC64A, V.EcoDcm from *E. coli*, V.HpaII from *Haemophilus parainfluenzae*, V.NeaI from *Nocardia aerocolonigenes* and V.XorII from *Xanthomonas oryzae*.

Alternatively, the single-strand nicks may also be introduced into the double-stranded polynucleotides by sequence-unspecific nicking enzymes. In this case, it is possible to use DNase I from calf pancreas with $Mg^{2+}$ as co-factor (Kunitz, J. Genetic Physiology 33 (1950), 349; Kunitz, J. Genetic Physiology 33 (1950), 363 and Melgac and Goldthwaite, J. Biolog. Chem. 243 (1968), 4409).

In another preferred embodiment, in the case of inserting single-strand nicks, there is subsequently an exonucleolytic single-strand degradation according to step (c) in 5'-3' direction of the method starting at the single-strand nicks. In this case, again, for example, the T7-exonuclease Gene 6 from the bacteriophage T7 can be used. Moreover, unpaired segments of the heteroduplexes are preferred to be exonucleolytically degraded by exonuclease VII from *E. coli*.

In another preferred embodiment of the method of the invention, in the case of inserting single-strand nicks, there is subsequently an exonucleolytic single-strand degradation according to step (c) of the method in 3'-5' direction starting at the single-strand nicks. In this case, exonuclease III from *E. coli* is preferred to be used. Preferably, in addition, unpaired segments of the heteroduplexes are exonucleolytically degraded in 3'-5' direction, e.g. by exonuclease I from *E. coli*.

In another preferred embodiment of the method of the invention, in the case of inserting single-strand nicks, there is subsequently an exonucleolytic single-strand degradation according to step (c) both in 5'-3' direction and in 3'-5' direction starting at the single-strand nicks. In this case, the aforementioned enzymes can be used. Preferably, the Bal31-nuclease derived from the culture medium of *Alteromonas espejiana* Bal31 is used. Furthermore, preferably unpaired segments of the heteroduplexes are exonucleolytically degraded by exonuclease VII from *E. coli*.

In another preferred embodiment of the method of the invention, a polymerase with 5'-exonucleolytic activity is used for the 5'-exonucleolytic degradation according to step (c) of the method of the invention, in particular after insertion of single-strand nicks.

Finally, the semi-conservative synthesis of the polynucleotides according to step (d) of the method of the invention is carried out by extending anew the 3'- or the 5'-end of the partially degraded single strand by means of a polymerase and the corresponding 5'- or 3'-segment of the complementary strand of the heteroduplex as template. The term "semi-conservative single-strand synthesis" means the synthesis of a polynucleotide by extending an existing single-strand by means of the information of a corresponding template strand.

Depending on the embodiment, only one of the two strands (e.g. codogenic or non-codogenic strand) is extended (embodiment A) or both strands are used as a template with the 5'- or the 3'-end. At the same time, they are synthesized anew at the 3'- or 5'-end (embodiment B). In embodiment B, the semi-conservative synthesis of the polynucleotides may be followed by a single synthesis of the complementary polynucleotides. Thereby, an efficient new combination of the conservative sequence segment that has not been degraded is achieved (cf. FIG. 4). The person skilled in the art is familiar with carrying out the template-directed polymerization, which is described, for instance, in Sambrook (Molecular Cloning, Cold Spring Harbor Laboratory Press (1989)) or Ausubel (ibid.).

For the polymerase reaction any enzyme with template-directed polynucleotide-polymerization activity can be used which is able to polymerize polynucleotide strands starting from the 3'- or the 5'-end. A vast number of polymerases from the most varied organisms and with different functions have already been isolated and described. With regard to the kind of the template and the synthesized polynucleotide, a differentiation is made between DNA-dependent DNA polymerases, RNA-dependent DNA polymerases (reverse transcriptases), DNA-dependent RNA polymerases and RNA-dependent RNA polymerases (replicases). With regard to temperature stability, it is differentiated between non-thermostable (37° C.) and thermostable polymerases (75–95° C.). In addition, polymerases differ with regard to the presence of 5'-3'- and 3'-5'-exonucleolytic activity. DNA-dependent DNA polymerases are the most important polymerases.

In particular, DNA polymerases with a temperature optimum of exactly or around 37° C. can be used. These include, for instance, DNA polymerase I from *E. coli*, T7 DNA polymerase from the bacteriophage T7 and T4 DNA polymerase from the bacteriophage T4 which are each traded by a large number of manufacturers, e.g. USB, Roche Molecular Biochemicals, Stratagene, NEB or Quantum Biotechnologies. The DNA polymerase I from *E. coli* (holoenzyme) has a 5'-3' polymerase activity, a 3'-5' proofreading exonuclease activity and a 5'-3' exonuclease activity. The enzyme is used for in vitro labelling of DNA by means of the nick-translation method (Rigby et al. (J. Mol. Biol. 113 (1977), 237–251)). In contrast to the holoenzyme, the Klenow fragment of DNA polymerase I from *E. coli* does also not have a 5'-exonuclease activity, just like the T7 DNA polymerase and the T4 DNA polymerase. Therefore, these enzymes are used for so-called filling-in reactions or for the synthesis of long strands (Young et al. (Biochemistry 31 (1992), 8675–8690), Lehman (Methods Enzymol. 29 (1974), 46–53)). After all, the 3'-5'-exo(–) variant of the Klenow fragment of DNA polymerase I from *E. coli* does also not have the 3'-exonuclease activity. This enzyme is often used for DNA sequencing according to Sanger (Sanger (Proc. Natl. Acad. Sci. USA 74 (1977), 5463–5467)). Apart from these enzymes, there is a plurality of other 37° C. DNA polymerases with different properties which can be employed in the method of the invention.

The most widespread thermostable DNA polymerase that has a temperature optimum of 75° C. and is still sufficiently stable at 95° C. is the Taq DNA polymerase from *Thermus aquaticus*, which is commercially available. The Taq DNA polymerase is a highly-processive 5'-3' DNA polymerase without 3'-5'-exonuclease activity. It is often used for standard PCRs, for sequencing reactions and for mutagenic PCRs (Cadwell and Joyce (PCR Methods Appl. 3 (1994), 136–140, Arigoni and Kaminski (Methods Mol. Biol. 23 (1993), 109–114)). The Tth DNA polymerase from *Thermus thermophilus* HB8 and the Tfl DNA polymerase from *Thermus flavus* have similar properties. The Tth DNA polymerase additionally has an intrinsic reverse transcriptase (RT) activity in the presence of manganese ions (Cusi et al. (Biotechniques 17 (1994), 1034–1036)). Among the thermostable DNA polymerases without 5'- but with 3'-exonuclease activity, numerous of them are commerically available: Pwo DNA polymerase from *Pyrococcus woesei*, Tli, Vent or DeepVent DNA polymerase from *Thermococcus litoralis*, Pfx or Pfu DNA polymerase from *Pyrococcus furiosus*, Tub DNA polymerase from *Thermus ubiquitous*, Tma or UITma DNA polymerase from *Thermotoga maritima* (Newton and Graham, in: PCR, Spektrum Akad. Verlag Heidelberg (1994), 1)). Polymerases without 3'-proofreading exonuclease activity are used for amplifying PCR products that are as free from defects as possible. After all, with the Stoffel fragment of Taq DNA polymerase, with Vent-(exo-) DNA polymerase and Tsp DNA polymerase thermostable DNA polymerases without 5'- and without 3'-exonucleolytic activity are available.

Among RNA-dependent DNA polymerases (reverse transcriptases), the AMV reverse transcriptase from the avian myeloblastosis virus, the M-MuLV reverse transcriptase from the *Moloney murine* leukemia virus and the HIV reverse transcriptase from the human immunodeficieny virus are the most common enzymes which are also traded by various manufacturers such as NEB, Life Technologies, Quantum Biotechnologies. Like the HIV reverse transcriptase, the AMV reverse transcriptase has an associated RNase-H activity. This activity is significantly reduced in M-MuLV reverse transcriptase. Both the M-MuLV and the AMV reverse transcriptase do not have a 3'-5'-exonuclease activity.

The most common enzymes among DNA-dependent RNA polymerases include the RNA polymerase from *E. coli*, the SP6-RNA polymerase from *Salmonella typhimurium* LT2 infected with the bacteriophage SP6, the T3-RNA polymerase from the bacteriophage T3 and the T7-RNA polymerase T7 from the bacteriophage T7.

In a preferred embodiment of the method of the invention, the template strands in step (d) of the method are DNA molecules and a DNA-dependent DNA polymerase is used for the template-directed single-strand synthesis.

In a particularly preferred embodiment, a non-thermostable DNA polymerase is used, a polymerase with 5'- and 3'-exonucleolytic activity, like polymerase I from *E. coli*, is particularly preferred.

Alternatively, also a non-thermostable DNA polymerase may be used which does not have a 5'-exonucleolytic activity but a 3'-exonucleolytic activity, e.g. the Klenow fragment of DNA polymerase I from *E. coli*, the T7-DNA polymerase from the bacteriophage T7 or the T4-DNA polymerase from the bacteriophage T4.

Furthermore, a non-thermostable DNA polymerase may be used which has neither a 5'- nor a 3'-exonucleolytic activity, e.g. the 3'-5'-exo(–) variant of the Klenow fragment of DNA polymerase I from *E. coli*.

In another particularly preferred embodiment, use is made of a thermostable polymerase (e.g. Taq-Pol, Pwo-Pol, etc.). This polymerase, again can have a 5'- and a 3'-exonucleolytic activity or a 5'-exonucleolytic activity, but no 3'-exonucleolytic activity, like, for example, the Taq DNA polymerase from *Thermus aquaticus*, the Tth DNA polymerase form *Thermus thermophilis* HB8 or the Tfl-DNA polymerase from *Thermus flavus*.

Alternatively, the thermostable DNA polymerase can have no 5'- but a 3'-exonucleolytic activity, like the Pwo-DNA polymerase from *Pyrococcus woesei*, the VentR-DNA polymerase, the DeepVentR-DNA polymerase or the Tli-DNA polymerase from *Thermococcus litoralis*, the Pfu-DNA polymerase or the Pfx-DNA polymerase from *Pyrococcus furiosus* or Tma-DNA polymerase or UITma-DNA polymerase from *Thermotoga maritima*.

In additon, a thermostable polymerase can be used which has neither a 3'- nor a 5'-exonucleolytic activity, like the Stoffel fragment of the Taq-DNA polymerase from *Thermus aquaticus*, the Tsp-DNA polymerase or the exo(–) variant of the VentR-DNA polymerase or of the DeepVentR-DNA polymerase from *Thermococcus litoralis*.

If a thermostable polymerase is used, the polymerase reaction is preferred to follow directly after the exonucleolytic degradation has been stopped, for instance, by raising the temperature. There is no purification in between or further treatment of the samples. Moreover, in the case of several cycles, it is preferably avoided to add polymerase anew after each round of purification. If an exonuclease is used which denatures when heated to a temperature of ≦72° C., but which is, however, renatured after thermal melting of the strands at about 90° C. and cooling down below the annealing temperature, an embodiment is possible that works as a one-pot reaction over several cycles without addition of substances or sample manipulation in between. In another preferred embodiment, exonuclease is added in excess relative to polymerase, wherein the processivity of polymerase (Pol I, etc.) is significantly higher than the one of the exonucleolytic degradation.

In another preferred embodiment, the 3'-ends of the newly synthesized segments are covalently coupled if single-strand nicks have been inserted before the exonucleolytic degradation and the subsequent template-directed single-strand synthesis. Preferably, said coupling is carried out by means of a ligase, particularly preferably with the T4-DNA ligase from the bacteriophage T4.

In another preferred embodiment of the method of the invention, the template strands in step (d) of the method of the invention at which the template-directed single-strand synthesis takes place are RNA molecules. In this case, an RNA-dependent DNA polymerase, preferably AMV reverse transcriptase from the avian myeloblastosis virus, HIV reverse transcriptase from the human immunodeficiency virus or M-MuLV reverse transcriptase from the *Moloney murine* leukemia virus are used for the template-directed single-strand synthesis. Furthermore, a thermostable reverse transcriptase is preferred to be used, the Tth-DNA polymerase from *Thermus thermophilus* with intrinsic reverse transcriptase activity is particularly preferred.

In another preferred embodiment, the polynucleotide strand, which, according to step (c), is subjected to the exonucleolytic single-strand degradation and, according to step (d) to the single-strand synthesis, consists of RNA.

Thus, the newly synthesized semi-conservative single-strand polynucleotides comprise the original information from the 5'- to the 3'-end or, as the case may be, from the 3'- to the 5'-end of the exonucleolytic degradation as well as the information of the counter strand from the 5'-end to the 3'-end or from the 3'-end to the 5'-end of the new synthesis. FIGS. 2 and 3 exemplarily show the possible embodiments A and B in the cyclical application (variant with 3'-exonucleolytic degradation). By controlling the length of the exonucleolytic single-strand degradation (e.g. time-controlled reaction of the exonucleolytic activity), in each cycle new combinations can be produced in a regio selective manner, i.e. preferably in particular sections of the polynucleotide sequences. By the cyclical application of said method, starting with another production of heteroduplex DNA of the semi-conservative single-strand molecules generated according to a first cycle, repeatedly new combinations may be produced. In this case, the cyclical application of embodiment A (cf. FIG. 2) offers both regio selective and ubiquitous combinations of different heterologous sequence segments with a defined recombination frequency of the polynucleotides. The cyclical application of embodiment B (cf. FIG. 3) offers the possibility of a complete new combination of the heterologous sequence segments of a quasi-species even after only a few cycles. In this case it has to be emphasized that the initial population of the polynucleotide strands does not serve as templates for newly synthesized polynucleotides, but that they are newly combined with each other according to a semi-conservative mechanism.

Therefore, the application of the method according to the invention makes it possible for two or more different heterologous sequence segments located on two different single-strand polynucleotides to be joined to new semi-conservative single-strand polynucleotides. By using said method, semi-conservative single-strand polynucleotides both with identical and different ratios of conservative and new sequence segments can be produced, depending on the controlled execution of the exonucleolytic degradation.

In addition, the present invention relates to a kit containing instructions for carrying out the method of the invention. In a preferred embodiment said kit also contains at least one of the following components:

(i) buffer for production of double-stranded polynucleotides;

(ii) agent permitting a partial exonucleolytic degradation of double-stranded polynucleotide molecules;

(iii) buffer for carrying out the partial exonucleolytic degradation;

(iv) agent permitting the template-directed polymerization of a polynucleotide strand starting from the degraded end; and (v) buffer for carrying out the polymerization reaction of (v).

These and other embodiments are disclosed and obvious to a skilled person and embraced by the description and the examples of the present invention. Additional literature regarding one of the above-mentioned methods, means and applications, which can be used within the meaning of the present invention, can be obtained from the state of the art, for instance from public libraries for instance by the use of electronic means. This purpose can be served inter alia by public databases, such as the "medline", which are accessible via internet, for instance on the website of the National Center for Biotechnology Information the National Institutes of Health or the National Library of Medicine. Other databases and addresses are known to a skilled person and can be obtained from the internet through the use of internet search engines such as Lycos or Google. An overview of sources and information regarding patents and patent applications in biotechnology is contained in Berks, TIBTECH 12 (1994), 352–364.

All of the above cited disclosures of patents, publications and database entries are specifically incorporated herein by reference in their entirety to the same extent as if each such individual patent, publication or entry were specifically and individually indicated to be incorporated by reference.

BRIEF DESCRIPTION OF THE DRAWINGS

The Figures show:

FIG. 6 shows the employed mutants and the resulting recombinants with the mutations used as markers according to Example 1.

The following Examples serve to illustrate the invention.

In the experimental examples described below, standard techniques of recombination DNA technology were used that were described in various publications, e.g. Sambrook et al. (1989), Molecular Cloning: A Laboratory Manual, Cold Spring Harbor Laboratory, or Ausubel et al. (1987), Current Protocols in Molecular Biology 1987–1988, Wiley Interscience, which are incorporated herein in their entirety by reference. Unless otherwise indicated, restriction enzymes, polymerases and other enzymes were used according to the manufacturers specifications. Oligonucleotides were synthesized on a Perkin Elmer Expedite DNA synthesizer.

EXAMPLE 1

In-vitro Recombination of B. subtilis Subtilisin E Variants

This example demonstrates the controllability of the number of recombination events per gene by recombining variants of B. subtilis subtilisin E in a single cycle of the method according to embodiment B of the present invention.

A. Vector Construction

Vector p3 is a 6.8 kb E.coli-B.subtilis shuttle plasmid that was derived from pMK3 (ATCC 37314) by substituting the HindIII site in the multiple cloning site of pMK3 with a unique NheI site followed by substituting the 908 bp sequence between the two EcoRI sites with a 472 bp insert containing the Bacillus subtilis p43 promoter and a unique KpnI site. The orientation in p3 is such that the modified multiple cloning site (EcoRI SmaI BamHI SalI PstI NheI) is located downstream of the promoter. A 1.7 kb DNA sequence containing the apre gene (subtilisin E) together with a terminator sequence was PCR-amplified from the Bacillus subtilis genome using oligonucleotides P01 and P02 as primers:

P01 (Length: 67 nt, containing a KpnI site (underlined)):
5'-AGCGCGCGATTATGTAAAATATAAAGTGATAGC GGTACCTACTCTGMTTTTTT TAAAAGGAGAGGG-3' (SEQ ID NO:1)

P02 (Length: 54 nt, containing a PstI site (underlined)):
5'-GGTCTGCTTCTTCCAGCCCTCCTGGTA CTGCAGCCATCCGTCGATCATGGAA CG-3' (SEQ ID NO:2)

Figure 1:
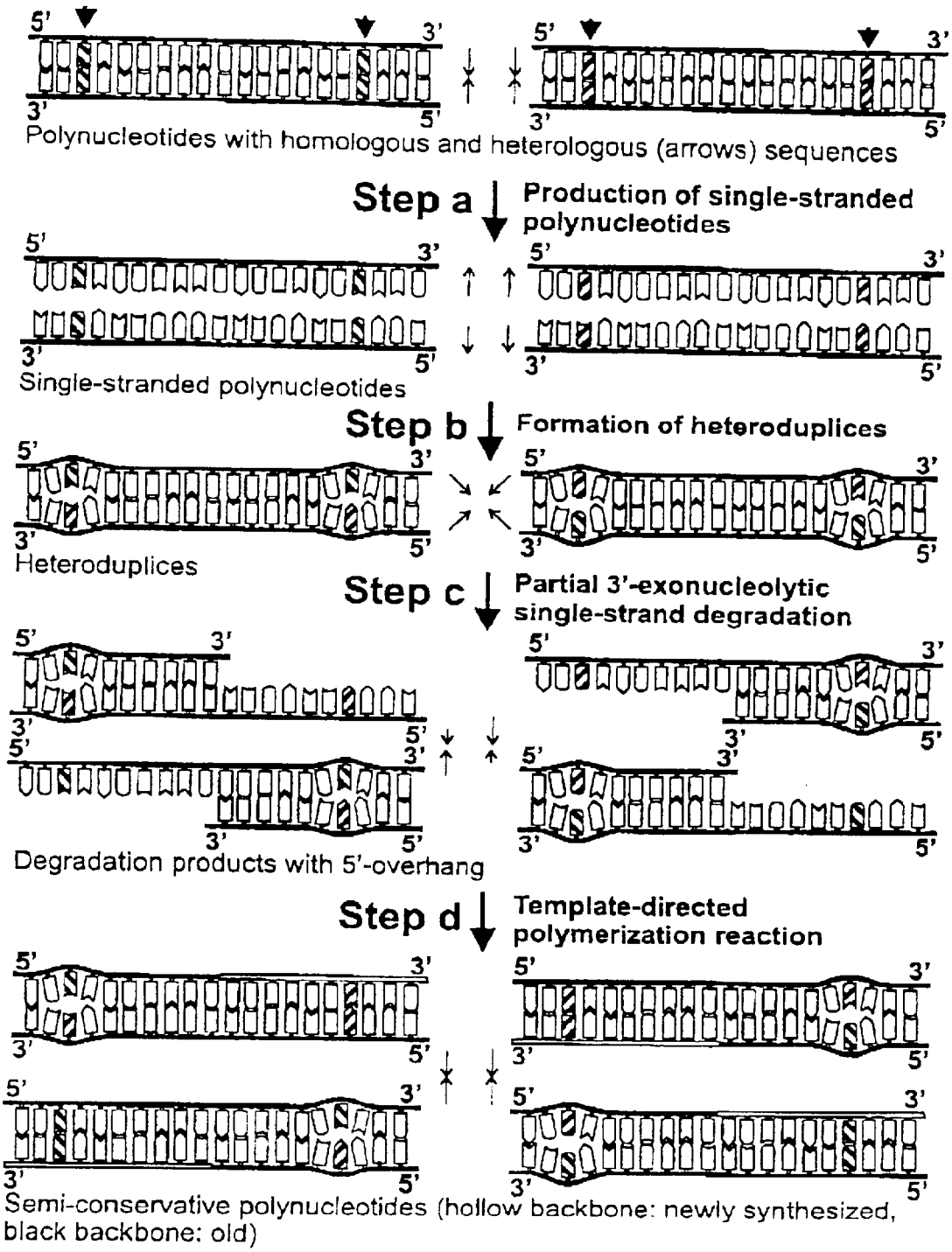
FIG. 1 is a schematic illustration of the method of the invention.
Figure 2:
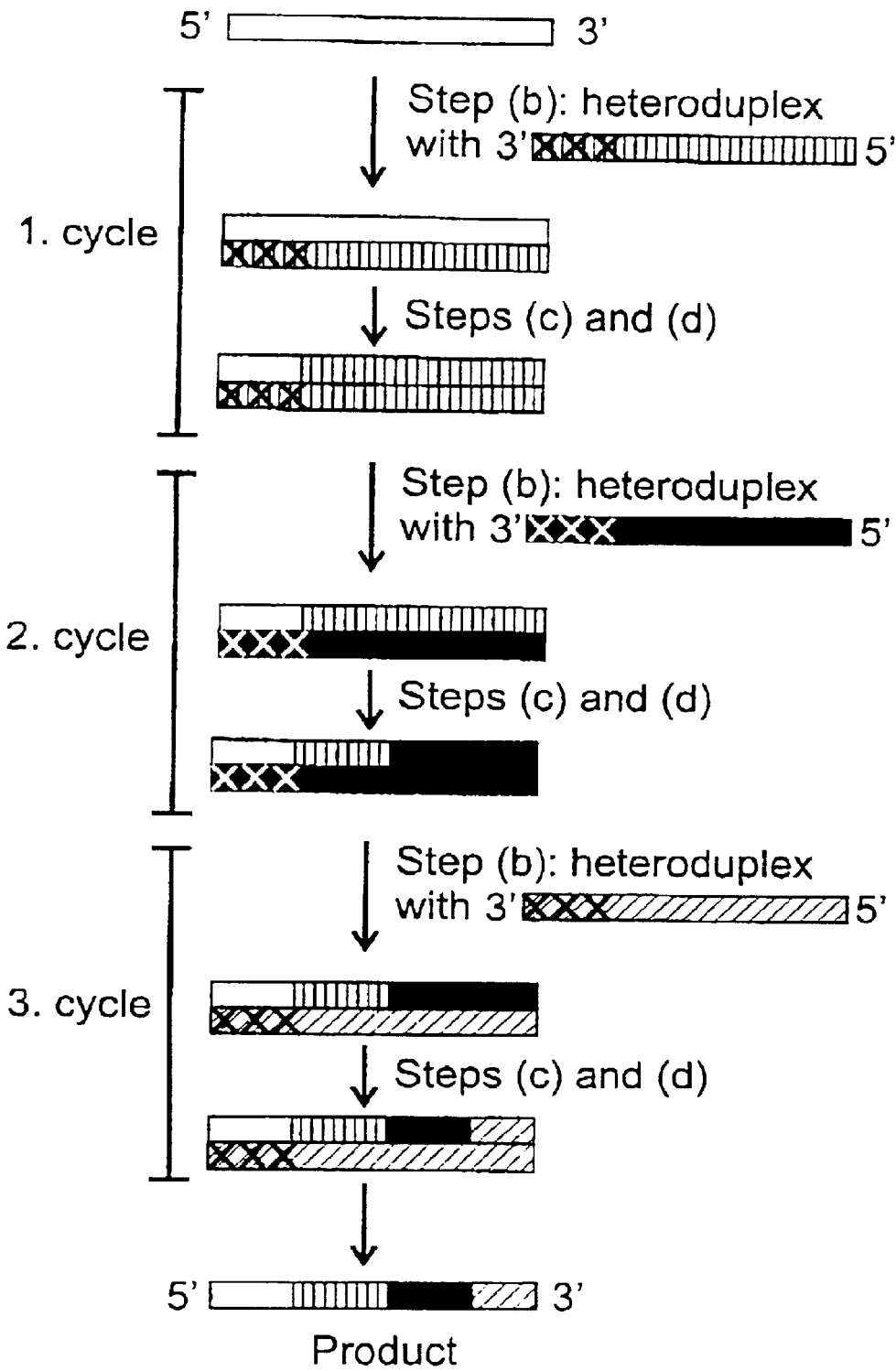
FIG. 2 illustrates the principle of the cyclical method of embodiment A of the method according to the invention with the template polynucleotides being protected from exonucleolytic degradation. Notation of steps is as defined in the text. For clarity only three cycles are shown.
Figure 3:
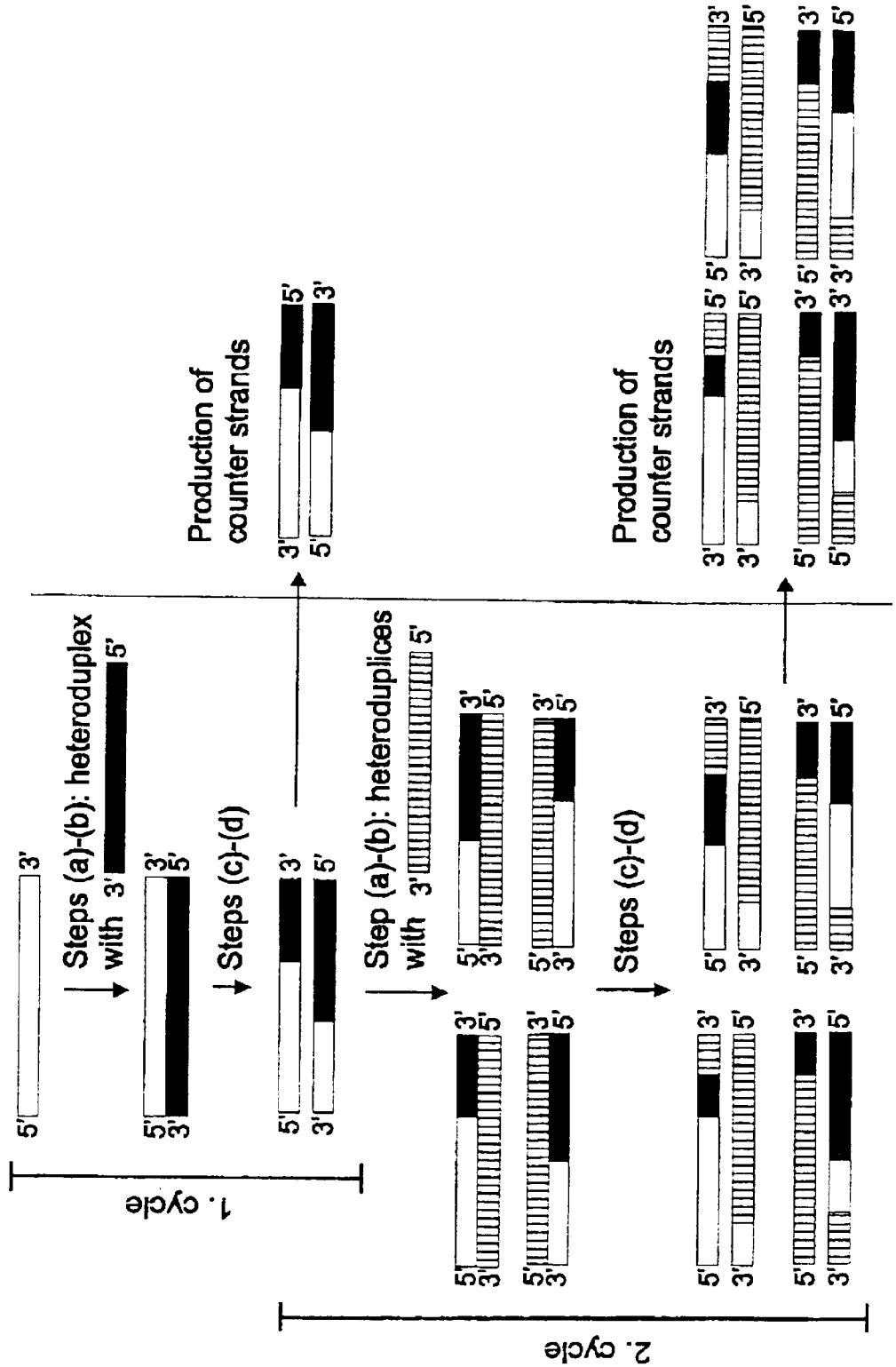
FIG. 3 illustrates the principle of the cyclical method of embodiment B of the method according to the invention in which each strand of a double-stranded polynucleotide serves as template and is degraded. Notation of steps is as defined in the text. For clarity only two cycles are shown.
Figure 4:
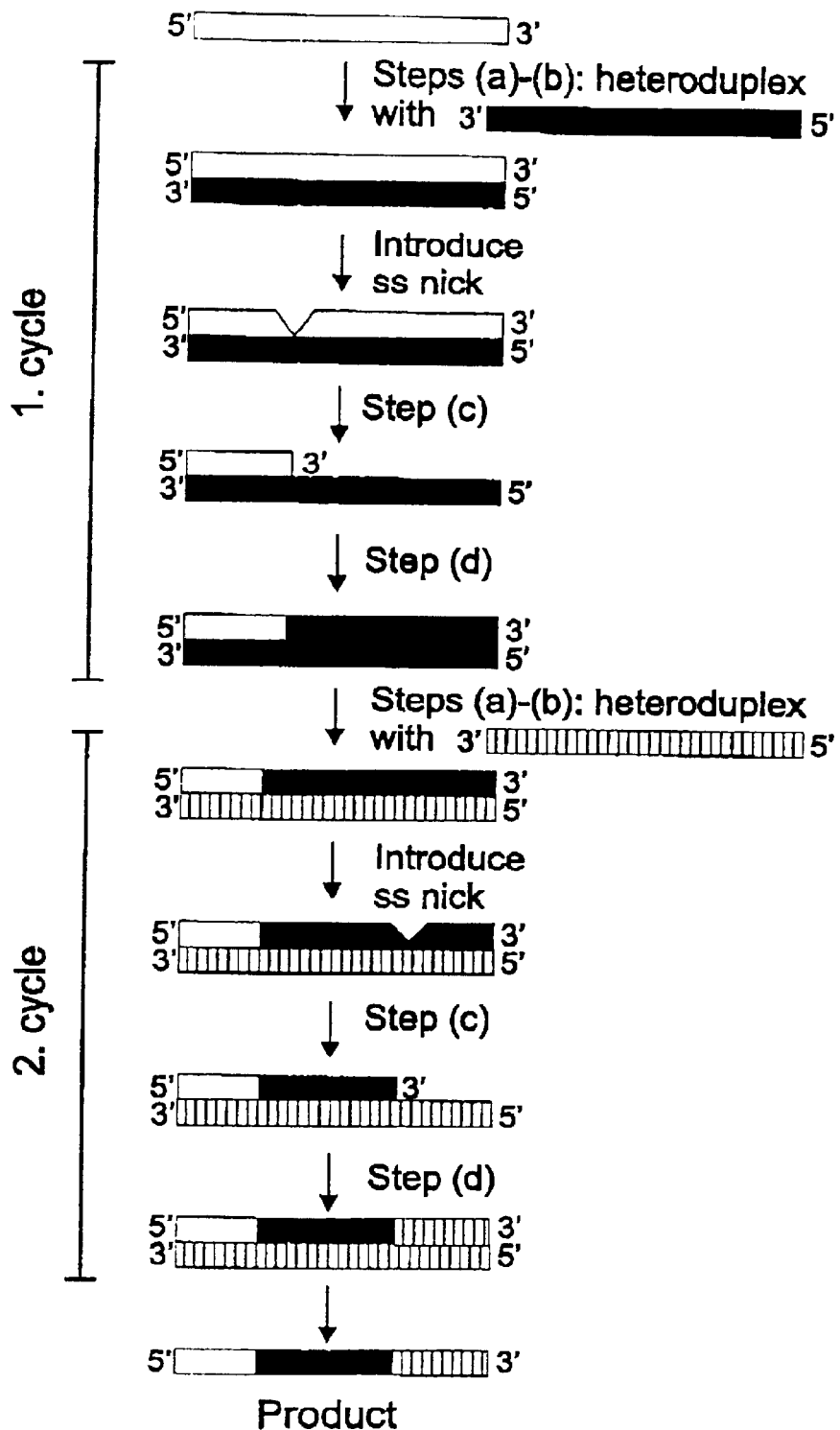
FIG. 4 illustrates the principle of the cyclical method of embodiment C of the method according to the invention in which single-strand nicks are inserted before the exonucleolytic degradation. Notation of steps is as defined in the text. For clarity only two cycles are shown. Exonucleolytic degradation proceeds from 5' to 3'.
Figure 5:
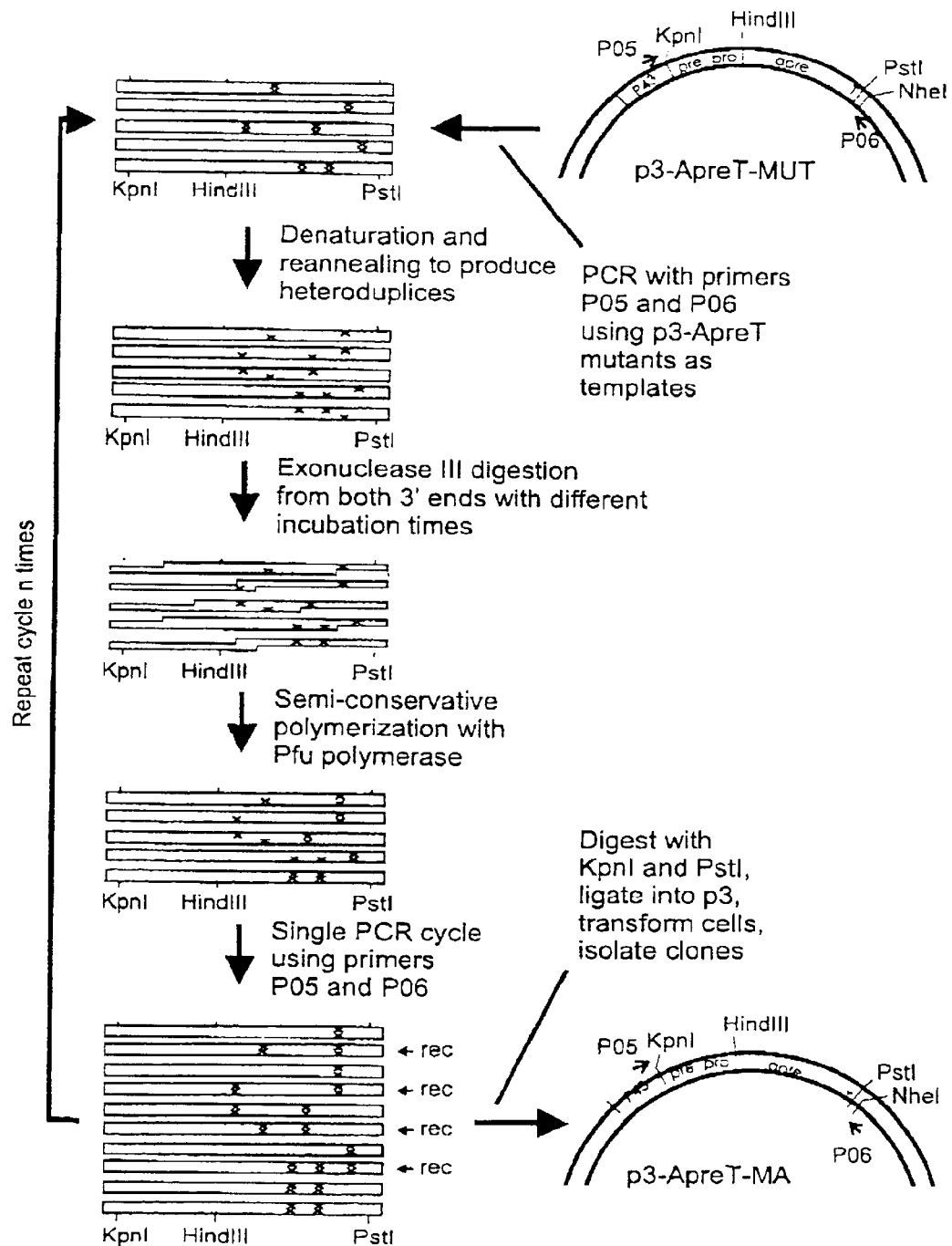
FIG. 5 illustrates schematically the procedure according to Example 1. However, in order to demonstrate the controllability of the number of recombination events in Example 1 the cycle is performed only once (n=0). For explanation see text, rec means recombinants.

The resulting PCR product was purified using the QIAquick PCR Purification Kit following the suppliers' instructions. After digestion with PstI and KpnI and agarose gel purification the PCR product was ligated into vector p3 which was digested with PstI and KpnI, gel-purified, and dephosphorylated, resulting in plasmid p3-ApreT (cf. FIG. 5). Transformation of a B. subtilis strain lacking the apre gene resulted in constitutive expression of subtilisin E. Activity was confirmed by plating transformants on LB Agar containing 1% skim milk resulting in cleared halos around each colony.

B. Mutant Generation

A 0.86 kb DNA sequence containing the apre sequence from the internal HindIII site to the C-terminal end of the gene was amplified from p3-ApreT by mutagenic PCR using oligonucleotides P03 and P04 as primers:

P03 (Length: 23 nt):
5'-GACTTAAACGTCAGAGGCGGAGC-3' (SEQ ID NO:3)

P04 (Length: 23 nt):
5'-GACCATGATTACGCCAAGCTAGC-3' (SEQ ID NO:4)

Figure 7:
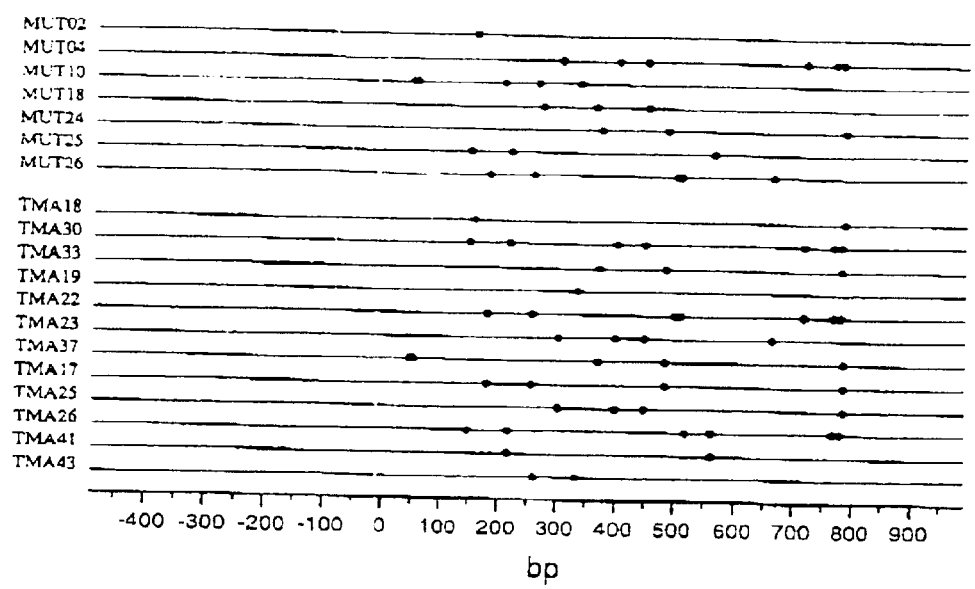
FIG. 7 shows the distribution of markers over the sequence for each mutant (MUT) as well as for each recombinant (TMA) according to Example 1. The KpnI site is at ca. −450 bp, the HindIII site at 0 bp, and the PstI site at ca. 900 bp.

Mutagenic PCR was done using 30 pmol of each primer, 20 nmol dGTP and dATP, 100 nmol dCTP and dTTP, 20 fmol template, and 5 U Taq DNA polymerase in 10 mM Tris HCl pH 7.6, 50 mM KCl, 7 mM $MgCl_2$, 0.5 mM $MnCl_2$, 0.01% gelatin for 20 cycles of 1 min at 94° C., 1 min at 65° C. and 1 min at 72° C. The resulting library was purified using the QIAquick PCR Purification Kit following the suppliers' instructions. After digesting the PCR products with HindIII and PstI and agarose gel purification they were ligated into p3-ApreT which was also digested with HindIII and PstI, gel-purified from the original apre insert, and dephosphorylated. Resulting clones were analyzed for subtilisin E activity by plating B. subtilis transformants on LB Agar containing 1% skim milk. Plasmids of seven clones showing no activity (p3-ApreT-MUT02, 04, 10, 18, 24, 25, 26) were isolated and sequenced. Sequence deviations of these inactive subtilisin E mutants from the wild type are shown in FIG. 6. Each of the mutant clones carries at least one mutation, and no mutation was formed twice. Altogether, the seven clones carry 26 mutations that can serve as markers that are randomly distributed over the sequence between the HindIII and the PstI site (cf. FIG. 7).

C. In-vitro Recombination 1.4 kb DNA sequences including the KpnI and the PstI cloning sites and the whole apre gene were PCR-amplified from each of the p3-ApreT-MUT clones using Pfu polymerase from Stratagene following the suppliers' directions and oligonucleotides P05 and P06 as primers:

P05 (Length: 20 nt):
5'-AATGGGCGTGAAAAAAAGCG-3' (SEQ ID NO:5)

P06 (Length: 23 nt):
5'-CCTGTGTGAAATTGTTATCCGCT-3' (SEQ ID NO:6)

PCR products were purified using the QIAquick PCR Purification Kit following the suppliers' instructions, checked for correct size by agarose gel electrophoresis and mixed together in equimolar amounts. 80 µg of this PCR mix in 150 mM TrisHCL pH 7.6, 6.6 mM $MgCl_2$ were heated for 5 min at 94° C. and subsequently cooled down to 37° C. at 0.05° C./sec in order to re-anneal strands and thereby produce heteroduplexes in a stochastic manner. Then, 2.5 U Exonuclease III per µg DNA were added and incubated for 20, 40 or 60 min at 37° C. in order to digest different lengths from both 3' ends of the heteroduplexes. The partly digested PCR products were refilled with 0.6 U Pfu polymerase per µg DNA (semiconservative polymerization) by incubating for 15 min at 72° C. in 0.17 mM dNTPs and Pfu polymerase buffer according to the suppliers' instructions. Performing a single PCR cycle using primers P05 and P06, the resulting DNA was purified using the QIAquick PCR Purification Kit following the suppliers' instructions, digested with KpnI and PstI, ligated into p3 linearized with KpnI and PstI and transformed into E. coli XL1-blue. Transformants were checked for carrying an insert by plasmid mini preparation and gel electrophoresis. From clones showing the correct size, 25 clones were randomly chosen, isolated and analyzed by sequencing.

D. Results

From the 25 randomly chosen clones 12 were recombinants and 13 were identical to the employed mutants, the distribution of which being rather stochastical. Two mutants were found four times (MUT04, MUT26), one mutant twice (MUT10), three mutants once (MUT18, MUT24, MUT25) and one mutant was not found (MUT02). Each of the 12 recombinants was found only once, clearly resulting from a single recombination event (cf. Table below). Without separation of samples from different Exonuclease III incubation times (20, 40 and 60 min), recombination sites can be found distributed over the whole sequence as demonstrated in FIG. 7. Altogether 48% recombinants were found. However, this number represents only the lower limit for the fraction of recombinants. Some or all of the apparently non-recombined mutants that were found may have originated from a recombination event that didn't change the sequence, mainly due to the fact that markers were only introduced in the C-terminal half of the gene (cf. FIG. 5).

TABLE

| recombinant | parental mutants | | recombination site is between position | | |
|---|---|---|---|---|---|
| TMA17 | MUT26 | x MUT24 | | 370 and | 484 |
| TMA18 | MUT02 | x MUT24 | " | 484" | 785 |
| TMA19 | wt[1] | x MUT10 | " | 261" | 334 |
| TMA22 | MUT26 | x MUT04 | " | 508" | 663 |
| TMA23 | MUT04 | x MUT26 | " | 508" | 663 |
| TMA25 | MUT04 | x MUT24 | " | 484" | 785 |
| TMA26 | MUT25 | x MUT04 | " | 717" | 767 |
| TMA30 | MUT25 | x MUT04 | " | 303" | 399 |
| TMA33 | MUT24 | x MUT04 | " | 767" | 780 |
| TMA37 | MUT10 | x MUT24 | " | 53" | 203 |
| TMA41 | wt[1] | x MUT25 | " | 148" | 216 |
| TMA43 | wt[1] | x MUT10 | " | 203" | 261 |

[1]"wt" means that the parental sequence is equal to wild type, i.e. carries no marker in the specific region

EXAMPLE 2

Exonuclease III Digestion

DNA digestion with Exonuclease III according to claim 9 is known from literature. However, the accuracy of the relation between incubation time and length of the digested DNA strand has mostly been analyzed with rather long DNA molecules, i.e. linearized plasmids. In order to demonstrate that shorter DNA molecules can be digested to a certain length also, a 0.8 kb PCR product representing a typically short open reading frame was digested with Exonuclease III. Resulting DNA molecules are partially double-stranded and partially single-stranded. In order to analyze sizes on an agarose gel, however, the molecules have to be purely double-stranded. Therefore, the single-stranded portion was digested by S1 Nuclease solely for analytical purposes, and the resulting distribution of undigested double stranded DNA molecules was analyzed via gel electrophoresis. If digestion is done from both 3' ends simultaneously, this leads to two superimposed length distributions.

Figure 8:
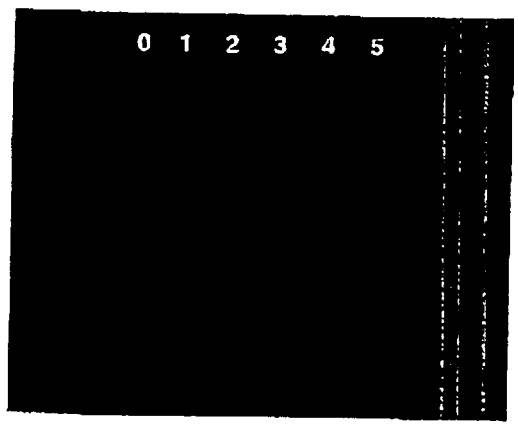
FIG. 8 shows the agarose gel image of DNA exonucleolytically digested for different incubation times (0=0 min, 1=1 min, 3=3 min, 4=4 min, 5=5 min) according to Example 2.

A. Method 0.75 μg of a 790 bp PCR-product were incubated with 200 Units Exonuclease III in 20 μl buffer containing 66 mM Tris-HCl, pH 8.0, 0.66 mM $MgCl_2$, 75 mM NaCl at 25° C. After 0, 1, 2 , 3, 4, and 5 min 2 μl samples were removed from the mixture, immediately mixed with 7.5 μl of S1 nuclease digestion mix (40.5 mM Na acetate, pH 4.6, 338 mM NaCl, 1.4 mM $ZnSO_4$, 6.8% glycerol, 1.88 U S1 nuclease), and placed on ice. After taking all samples, tubes were incubated at room temperature for 30 min. S1 nuclease was inactivated by adding 1 μl stop solution (300 mM Tris; 50 mM EDTA, pH 8.0) and incubating samples for 10 min at 70° C. Samples were assayed on a 2% agarose gel stained with Ethidium bromide and analyzed under UV light B. Results Results of the digestion are shown in FIG. 8. The numbers correspond to the incubation time in minutes. Under these reaction conditions, digestion proceeds almost linearly with a velocity of about 25 nucleotides per min. The lengths corresponding to a certain incubation time are not precisely defined, but show a Gaussian-like distribution with a standard deviation of about 50 nucleotides, enabling both, on the one hand the focussing of the recombination site to a certain region in the sequences to be recombined, and, on the other hand, e.g. by mixing samples from different incubation times, the regio-unspecific recombination over the complete sequence.

What is claimed is:

1. A method for the production of polynucleotide molecules with modified properties, wherein at least one cycle comprising the following steps is completed:

(a) providing a population of single-stranded polynucleotide molecules, wherein individual single-stranded polynucleotide molecules comprise homologous and heterologous sequence seqments and wherein individual ones of said single-stranded polynucleotide molecules can form double-stranded polynucleotide molecules with other ones of said single-stranded polynucleotide molecules within said population;

(b) forming double-stranded polynucleotide molecules from the population of single-stranded polynucleotide molecules provided according to step (a) comprising double-stranded polynucleotide molecules with different heterologous sequence segments;

(c) partially and exonucleolytically degrading the single-strands of the double-stranded polynucleotide molecules produced according to step (b); and (d) template-directed single-strand synthesizing the degraded ends of the partially degraded double strand produced according to step (c), wherein steps (c) and (d) may be carried out sequentially or contemporaneously.

2. The method according to claim 1, wherein more than one cycle comprising steps (a) to (d) is completed.

3. The method according to claim 2, wherein the degradation length of the exonucleolytic degradation, according to step (c) of the method of the invention is constantly reduced with increasing number of cycles.

4. The method according to any one of claims 1 to 3, wherein reglo selectivity of the combination of partially degraded and newly synthesized strands is regulated by the control of the partial, exonucleolytic single-strand degradation according to step (c).

5. The method according to claim 2, wherein after one, several or all cycles a selection step is carried out, and said selection step relates to either the genotype or the phenotype or to both the genotype and the phenotype of the polynucleotide.

6. The method according to claim 1, wherein the population of single-stranded polynucleotide molecules provided according to step (a) are polynucleotide molecules from the mutant distribution of a quasi-species.

7. The method according to claim 1, wherein the polynucleotide stand subjected to an exonucleolytic single-strand degradation and single-strand synthesis consists of DNA.

8. The method according to claim 1, wherein the exonucleolytic single-strand degradation of the double-stranded polynucleotides according to step (c) takes place in 3'-5' direction.

9. The method according to claim 8, wherein in step (c) exonuclease III from E. coli is used for the 3'-exonucleolytic single-strand degradation.

10. The method according to claim 8 or 9, wherein in step (c) exonuclease I from E. coli is used for the 3-exonucleolytic single-strand degradation of unpaired segments of the heteroduplexes.

11. The method according to claim 1, wherein the exonucleolytic single-strand degradation of the double-stranded polynucleotides; according to step (c) takes place in 5'-3' direction.

12. The method according to claim 11, wherein in step (c) T7-exonuclease Gene 6 from the bacteriophage T7 is used for the 5'-exonucleolytic single-strand degradation of the double-stranded polynucleotides.

13. The method according to claim 11 or 12, wherein in step (c) exonuclease VII from E. coli is used for the 5'-exonucleolytic single-strand degradation of unpaired segments of the heteroduplexes.

14. The method according to claim 1, wherein one of the two ends of the polynucleotide double-strand is modified in such a way that it is protected from the 3'- or 5'-exonucleolytic single-strand degradation according to step (c).

15. The method according to claim 14, wherein the modification takes place by selective insertion of thioesters or by cleavage with a restriction enzyme leading to a 3'-overhang, or by first providing one of the two strands as circular single strand, or by covalent coupling with a compatible, circular polynucleotide molecule.

16. The method according to claim 1, wherein before the exonucleolytic single-strand degradation according to step (c), single-strand nicks are introduced into the double-stranded polynucleotide molecules.

17. The method according to claim 16, wherein on average one or less than one single-strand nick per double-stranded polynucleotide molecule is introduced.

18. The method according to claim 16 or 17, wherein single-strand nicks are introduced into the double-stranded polynucleotide molecules by means of sequence-specific nicking enzymes.

19. The method according to claim 16 or 17, wherein single-strand nicks are introduced into the double-stranded polynucleotide molecules by means of sequence-specific nicking enzymes.

20. The method according to claim 16, wherein the exonucleolytic single-strand degradation according to step (c) takes place both in 5'-3' direction and in 3'-5' direction.

21. The method according to claim 20, wherein Bal31-nuclease from the culture medium of *Alteromonas espejiana* Bal31 is used for the contemporaneous 5'- and 3'-exonucleolytic single-strand degradation in step (c).

22. The method according to claim 16, wherein the exonucleolytic single-strand degradation according to step (c) takes place by means of a polymerase with 5'-exonucleolytic activity.

23. The method according to claim 7, wherein the template strands in step (d) are DNA molecules and one or more DNA-dependent DNA polymerases are used for the template-directed single-strand synthesis.

24. The method according to claim 23, wherein polymerase I from *E. coli* is used.

25. The method according to claim 23, wherein one or several thermostable DNA polymerases are used.

26. The method according to claim 25, wherein Taq DNA polymerase from *Thermus aquaticus*, Tth DNA polymerase from *Thermus thermophilus* HB8 or Tfl DNA polymerase from *Thermus flavus* is used.

27. The method according to claim 16, wherein the 3'-ends of the newly synthesized segments are covalently coupled with the 5'-ends of the segments partially degraded in an exonucleolytic manner.

28. The method according to claim 27, wherein the covalent coupling takes places by means of T4 DNA ligase from the bacteriophage T4.

29. The method according to claim 7, wherein the template strands in step (d) are RNA molecules and one or more RNA-dependent DNA polymerases are used for the template-directed single-strand synthesis.

30. The method according to claim 29, wherein AMV reverse transcriptase from the avian myeloblastosis virus, HIV reverse transcriptase from the human immunodeficiency virus, M-MuLV-reverse transcriptase from the Moloney murine leukemia virus or Tth DNA polymerase from *Thermus thermophilus* with intrinsic reverse transcriptase activity are used.

31. The method according to claim 1, wherein the polynucleotide strand subjected to exonucleolytic single-strand degradation and single-strand synthesis consists of RNA.

\* \* \* \* \*